United States Patent
Broome

[19]

[11] Patent Number: 5,980,454
[45] Date of Patent: Nov. 9, 1999

[54] ENDOSCOPIC IMAGING SYSTEM EMPLOYING DIFFRACTIVE OPTICAL ELEMENTS

[75] Inventor: Barry Broome, Glendora, Calif.

[73] Assignee: Endonetics, Inc., San Diego, Calif.

[21] Appl. No.: 08/982,305

[22] Filed: Dec. 1, 1997

[51] Int. Cl.$^6$ .............................. A61B 1/07; G02B 27/44
[52] U.S. Cl. .......................... 600/176; 600/177; 600/182; 359/565; 359/615
[58] Field of Search .................................... 600/108, 129, 600/160, 167, 174, 175, 176, 177, 178; 359/652, 654, 565, 615, 19; 385/33, 119

[56] References Cited

U.S. PATENT DOCUMENTS

| | | |
|---|---|---|
| 3,814,498 | 6/1974 | Tomlinson, III et al. . |
| 3,818,902 | 6/1974 | Kinoshita ................................. 600/177 |
| 4,111,529 | 9/1978 | Yamashita ............................... 600/176 |
| 4,350,149 | 9/1982 | Yamashita ............................... 600/177 |
| 4,704,007 | 11/1987 | Landre ..................................... 600/167 |
| 4,787,722 | 11/1988 | Clayton . |
| 4,798,446 | 1/1989 | Hettrick . |
| 4,824,225 | 4/1989 | Nishioka . |
| 4,834,070 | 5/1989 | Saitou ...................................... 600/108 |
| 4,916,534 | 4/1990 | Takahashi ............................... 600/171 |
| 4,936,666 | 6/1990 | Futhey . |
| 5,014,121 | 5/1991 | Hasegawa ................................. 358/55 |
| 5,044,706 | 9/1991 | Chen . |
| 5,132,843 | 7/1992 | Aoyama et al. . |
| 5,151,823 | 9/1992 | Chen ....................................... 359/565 |
| 5,257,133 | 10/1993 | Chen . |
| 5,261,904 | 11/1993 | Baker ....................................... 606/17 |
| 5,268,790 | 12/1993 | Chen ....................................... 359/565 |
| 5,305,736 | 4/1994 | Ito . |
| 5,331,950 | 7/1994 | Wood, Sr. . |
| 5,341,240 | 8/1994 | Broome . |
| 5,444,574 | 8/1995 | Ono ......................................... 359/708 |
| 5,491,765 | 2/1996 | Matsumoto . |
| 5,547,457 | 8/1996 | Tsuyuki ................................... 600/176 |
| 5,566,023 | 10/1996 | Kley ........................................ 359/565 |
| 5,619,380 | 4/1997 | Ogasawara et al. . |
| 5,627,679 | 5/1997 | Iba .......................................... 359/565 |
| 5,629,799 | 5/1997 | Maruyama et al. . |
| 5,629,800 | 5/1997 | Hamblen ................................. 359/565 |
| 5,704,896 | 1/1998 | Fukunishi ............................... 600/109 |
| 5,730,702 | 3/1998 | Tanaka .................................... 600/178 |
| 5,737,125 | 4/1998 | Ohashi .................................... 359/565 |
| 5,777,797 | 9/1998 | Miyano ................................... 600/176 |
| 5,800,343 | 2/1997 | Takeuchi ................................. 600/178 |
| 5,841,586 | 3/1997 | Nagaoka ................................. 359/654 |

OTHER PUBLICATIONS

Sommerfeld, "Phase Gratings", *Optics*, 1972, pp. 228–233.
Swanson et al, "Infrared applications . . . ", SPIE, 883, 155–162.
Faklis et al, "Optical Design with . . . ", Photonics Spectra, Nov. 1991, 205–208.
Miyamoto, "The Phase Fresnel Lens", JOSA, 51, 1, Nov. 1961, 17–20.
Faklis et al, "Diffractive Lenses . . . ", Photonics Spectra, Dec. 1991, 131–134.

*Primary Examiner*—John P. Leubecker
*Attorney, Agent, or Firm*—Michael de Angeli

[57] ABSTRACT

An improved endoscope comprises an objective including a diffractive optical element juxtaposed to a solid-state imaging element at the distal tip of the endoscope. An inexpensive halogen lamp at the proximal end of the endoscope is employed as the illumination source. A fiber-optic bundle carries light to the distal tip of the endoscope, where diffractive optical elements are provided to disperse light, illuminating the field of view.

53 Claims, 4 Drawing Sheets

ENDOSCOPIC IMAGING SYSTEM EMPLOYING DIFFRACTIVE OPTICAL ELEMENTS

FIELD OF THE INVENTION

This application relates to improved endoscopic imaging systems. In particular, the application relates to improved endoscopes employing diffractive optical elements in one or both of the objective and illuminator optics.

BACKGROUND OF THE INVENTION

Endoscopes, that is, instruments for viewing the interior of volumes not accessible to direct examination, are shown by prior art extending back many years. A number of different classes of endoscopes are shown in the prior art.

In a first class of endoscopes, an image formed by an objective at the distal tip of a rigid tubular member is transferred by a transfer module comprising a sequence of refractive optical elements to an image-forming device at the proximal end of the tube. See, for example, Broome U.S. Pat. No. 5,341,240. The image-forming device may include an optical eyepiece for direct viewing, or an electronic imaging device and associated circuitry for providing a visible image on an electronic display screen.

The prior art also teaches endoscopes wherein the image formed by an objective at the distal tip of the endoscope is transferred by a fiber optic bundle to an image-forming device at a proximal end of the endoscope. Employment of the fiber optic bundle in lieu of the refractive elements in a transfer module disposed in a rigid tube allows some flexibility of the shaft of the endoscope, which is of particular value in medical applications. However, the ultimate image quality is severely limited by the use of the fiber optic bundle to transfer the image from the objective to the image-forming device.

A third class of endoscopes is shown in, for example, U.S. Pat. No. 5,305,736 to Ito, wherein a solid state imaging element, typically a charge-coupled device (CCD) imaging element, is juxtaposed to the objective, so that an image signal is formed at the distal tip of the endoscope. As only wires are needed to transfer the image signal from the tip of the endoscope to means for display, the endoscope can be relatively flexible.

Ito also teaches the transmission of illuminating light from a source located at the proximal end of the endoscope to its distal tip by a fiber optic bundle. A dispersing optical element is provided at the tip of the fiber optical bundle, causing the light emitted by the fiber optic bundle to diverge, illuminating a relatively broad field of view.

In its preferred embodiment, the present invention relates generally to an endoscope of the class described in the Ito patent, that is, the present invention also relates to an endoscope wherein an image signal is formed by a solid state imaging element juxtaposed to the objective. Also as in Ito, an optical conduit, such as a fiber optic bundle, carries light from a source external to the proximal end of the endoscope to its distal tip, and a dispersive optical element is used to illuminate a wide field of view. However, the present invention makes numerous improvements over the endoscope shown in Ito, and certain aspects of the invention described herein have applicability beyond this preferred embodiment.

Other prior art references generally relevant to the subject matter of the present invention include Nishioka U.S. Pat. No. 4,824,225, teaching a particular illumination optical system for an endoscope. Nishioka teaches use of an aspheric lens for dispersing light from the distal tip of a fiber optic bundle, so as to illuminate a relatively wide field of view.

A number of additional patents also address the question of providing sufficient illumination to the field of view of an endoscope. See, for example, Matsumoto U.S. Pat. No. 5,491,765 showing a light source for an endoscope. The light source includes a parabolic reflector directing light from a lamp onto an aspheric element for focusing the light onto the input end of a fiber optic bundle, which then transmits the light to the distal tip of the endoscope for illuminating a field of view.

Wood U.S. Pat. No. 5,331,950 teaches a light source for an endoscope wherein a relatively low-powered metal halide arc discharge lamp is disposed at the focus of a reflector for concentrating light on the proximal end of a fiber optic bundle. This solution is technically useful in that such metal halide discharge lamps provide substantial illumination; however, such lamps require costly power supplies and are themselves relatively expensive.

It has been known for many years that, at least in theory, diffractive optical elements can be advantageously substituted for many types of refractive optical elements, for example, to focus light from a field of view in order to form an image. In this connection, a refractive optical element is one in which rays of light are bent at the interfaces between differing transmissive media. The degree of bending is proportional to the relative velocities of light in the two media, and is expressed by Snell's Law. Lenses in common use are typically refractive; for example, Ogasawara et al U.S. Pat. No. 5,619,380 discloses an objective for an endoscope employing refractive lens elements.

So-called "Fresnel" lenses are also refractive. In Fresnel lenses, the smooth surfaces of conventional refractive lenses are divided by grooves into a number of smaller areas, typically concentric circular zones, and the two optical surfaces of the lens are effectively collapsed toward one another. The advantage is that the overall thickness, weight, and cost of the lens are reduced. The width of the zones, i.e., the spacing of the grooves, is many hundreds of wavelengths of the light to be focused. Claytor U.S. Pat. No. 4,787,722 shows such Fresnel lenses.

By comparison, diffractive optical elements typically comprise a number of parallel lines or grooves spaced on the order of the wavelength of the light to be focused. Light rays are bent through an angle which varies as a function of the wavelength of the light and the spacing of the grooves. If the lines are spaced uniformly, the structure is commonly referred to as a diffraction grating, and the light is simply bent differentially as a function of wavelength; that is, white light is broken into its constituent colors. This phenomenon accounts for the spectral patterns seen when one inspects a structure including closely spaced grooves, such as the surface of a conventional "CD-ROM" optical storage device.

If the spacing of the grooves is varied, the diffractive effect may be used to form an image by bending light incident from various directions differentially, i.e., so that light from different parts of a field of view is directed onto corresponding portions of an image plane. Moreover, if the depth of the grooves is also varied, the diffraction efficiency (the amount of the incident light that is diffracted into a particular "order") can be optimized, to form a substantially uniformly illuminated image.

The basic theoretical underpinnings of diffractive optics are shown in numerous references. See, for example, Sommerfeld, *Optics*, Section D, "Phase Gratings", pages 228–233 (1964); Miyamoto, "The Phase Fresnel Lens", *JOSA*, Vol. 51, No. 1, pages 17–20 (1959); Swanson et al, "Infrared Applications of Diffractive Optical Elements", *SPIE Holographic Optics: Design and Applications*, Vol. 883, 155–162 (1988); Faklis et al, "Optical Design of Diffractive Lenses", *Photonics Spectra*, 205–208 (November 1991); Faklis et al, "Diffractive Lenses in Broadband Optical System Design", *Photonics Spectra*, 131–134 (December 1991).

Various U.S. patents teach diffractive lenses and other diffractive optical elements, both in general and for specific purposes. Tomlinson et al U.S. Pat. No. 3,814,498 teaches that by selecting the spacing and depth of grooves, an optical grating can be caused to focus light. Hettrick U.S. Pat. No. 4,798,446 is generally similar, as is Aoyama et al U.S. Pat. No. 5,132,843. Futhey U.S. Pat. No. 4,936,666 teaches specific improvements in manufacture of diffractive lenses. Three Chen patents, U.S. Pat. Nos. 5,151,823, 5,044,706, and 5,257,133, show various optical systems employing diffractive elements, none of these relating directly to endoscopes. Maruyama et al U.S. Pat. No. 5,629,799 discusses diffractive elements at some length, and provides specific designs for objectives using at least one diffractive element, in some cases provided over an underlying aspheric surface, for laser diode reading systems for optical disk drives. Finally, Baker U.S. Pat. No. 5,261,904 teaches a laser catheter for ablating atherosclerotic deposits in veins and the like, having a diffractive grating for beam shaping.

However, while as noted there exists ample technical literature relating to diffractive optical elements in general, and while various patents address specific systems employing such elements, no prior art presently known to the inventor discusses use of such diffractive elements in endoscopes per se.

Manufacture of a suitable endoscope involves consideration of numerous optical and related constraints. It will be apparent, of course, that substantial illumination must be provided by a lamp and dispersed into the field of view at the distal tip of the endoscope in order that the objective can collect sufficient light to form a useful image. In general, the more light delivered, the better the quality of the image. However, as noted, the brightest light sources available for such use, that is, short-arc lamps such as xenon lamps, or the metal halide lamps used in the Wood patent, are too expensive for certain uses. It would therefore be desirable to provide an optical system for an endoscope sufficiently efficient (including both the optics for transferring light from the source to the tip of the endoscope, and the image-forming objective) that a less expensive lamp could be used.

Reduction in cost of endoscopes is always desired; of course, in the medical context, reduction of cost means that an instrument will be affordable for use in more types of diagnostic and therapeutic procedures, which can ultimately lead to an improvement in patient care. Hence, it is significant to reduce the cost of the components employed in the endoscope.

Similarly, the smaller the endoscope the better, particularly for medical use, so as to be received into various cavities or incisions allowing the patient's anatomy to be examined. Given that larger optical elements are in general able to collect more light, to combine a relatively low cost illumination source with an efficient objective capable of collecting sufficient light to form high quality images while remaining small in diameter poses a significant technical challenge not met by any prior art endoscopes known to the inventor.

OBJECTS OF THE INVENTION

It is therefore a primary object of the invention to provide a relatively low cost endoscopic imaging system providing satisfactory image quality.

It is a more specific object of the invention to provide a relatively compact endoscope objective providing a wide angle of view and efficient light-gathering capability, and which can be manufactured in a cost-effective manner.

It is a further object of the invention to provide an improved endoscope employing diffractive optical elements to provide improved optical performance while allowing use of a low-cost illumination source, reducing cost.

It is a further object of the invention to provide an endoscope having improved image formation capability in a physical package sufficiently small to be useful in examination of very small structures.

SUMMARY OF THE INVENTION

The above objects of the invention and needs of the art are satisfied by the endoscopic imaging system of the invention. The objective of the endoscope of the invention in its preferred embodiment includes an optical element having a diffractive surface, providing sufficient light-gathering ability that a low-cost lamp can be employed as the light source for the system. The diffractive element is spaced a substantial distance from an aperture stop, allowing formation of an image. The diffractive surface allows a compact objective to be employed to form an image from a wide angle field of view. In the preferred embodiment a CCD imaging element is juxtaposed to the objective.

Several different objective designs including diffractive optical elements are disclosed, as is an all-glass refractive objective providing satisfactory light-gathering performance at slightly higher cost.

The proximal end of a single bundle of optical fibers is illuminated by a low-cost light source, e.g., a quartz-halogen lamp integrated with an elliptical reflector, so that the fibers convey light to the distal end of the endoscope. In a preferred embodiment, the distal end of the bundle of fibers is divided into two bundles, the tips of which are disposed on either side of the objective, to further improve the uniformity of illumination. Divergent optical elements, which may also be diffractive, are used to disperse light emitted from the tips of the fiber optic bundles at the distal tip of the endoscope, illuminating objects in a wide field of view.

BRIEF DESCRIPTION OF THE DRAWINGS

The invention will be better understood if reference is made to the accompanying drawings, in which.

DESCRIPTION OF THE PREFERRED EMBODIMENTS

Figure 1:
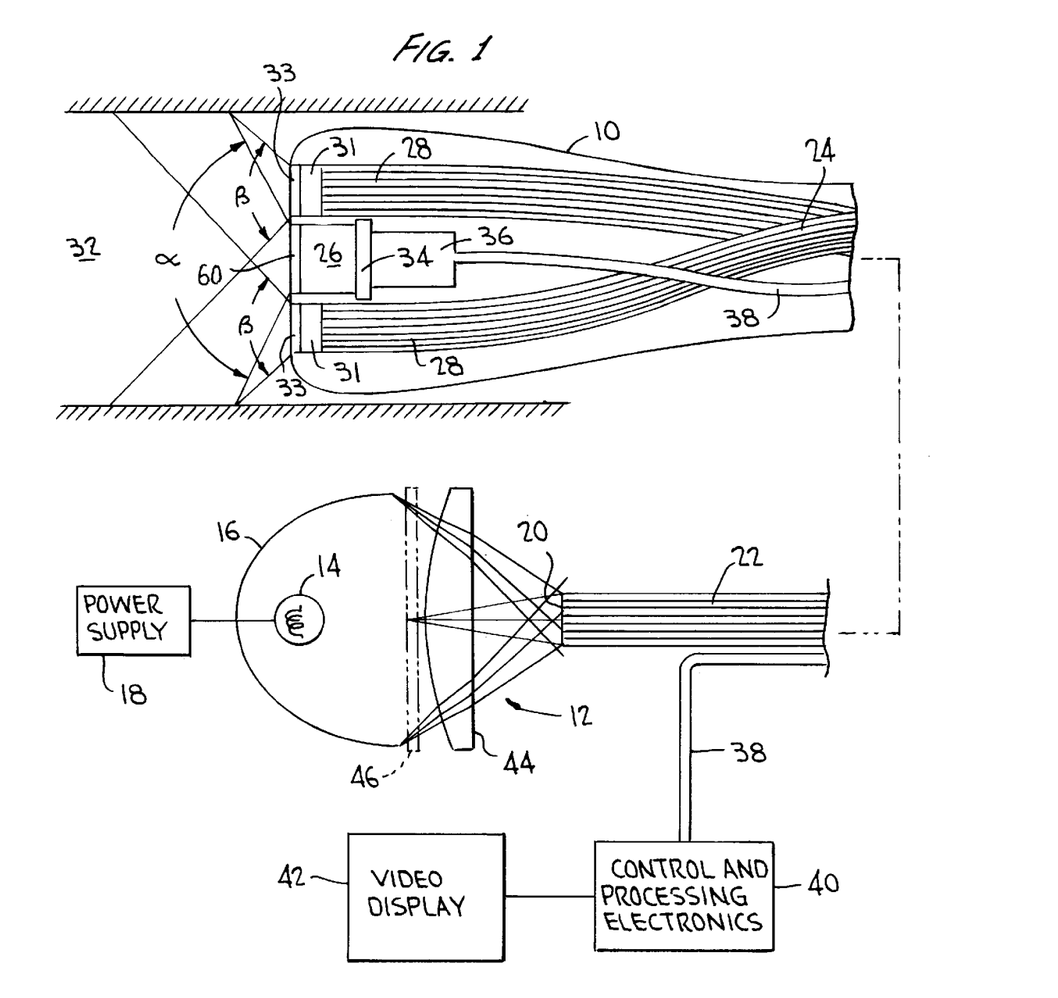
FIG. 1 shows a schematic overview of the endoscopic imaging system according to the invention.
Figure 2:
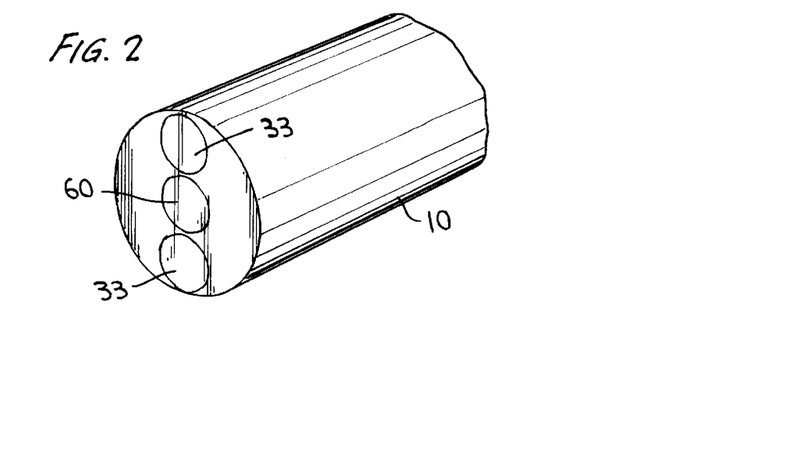
FIG. 2 shows an end view of the distal tip of the endoscope.

FIG. 1 shows as mentioned an overall view of an endoscopic imaging system according to the invention, comprising a probe extending from a distal tip 10 to a proximal end 12, while FIG. 2 shows a perspective view of the tip 10 of the probe. The probe may typically be up to eight feet long, but can be longer. A light source at the proximal end 12 comprises a lamp 14 driven by a power supply 18. Illumination provided by lamp 14 is directed by a reflector 16, ellipsoidal in this embodiment, onto the proximal end 20 of a bundle 22 of optical fibers. Lamp 14 and reflector 16 may be integral; a conventional quartz-halogen lamp may be used. Bundle 22 of optical fibers extends to the distal tip 10 of the probe; in the preferred embodiment, bundle 22 is divided into two bundles 28 at a branching point 24, so that the illumination provided is more uniformly distributed around the objective assembly 26.

As shown in FIGS. 1 and 2, a window 60 at the distal tip of the endoscope system according to the invention protects an objective assembly 26 discussed in detail below, and flanked on either side by the tips of the two bundles 28 of illuminating optical fibers. Divergent optical elements 31 protected by windows 33 are juxtaposed to the ends of the two bundles 28 of optical fibers to cause the light provided by fiber optic bundles 28 to diverge, illuminating objects in a wide field of view indicated generally at 32.

According to an important goal of the invention, the objective 26 collects light reflected from objects in a field of view defined by an angle α of at least about 135°. In order that objects in this field of view can be usefully imaged, the breadth of illumination provided by fiber optic bundles 28 must be commensurate therewith, as indicated by angles β in FIG. 1.

Thus, as illustrated in the view of the tip 10 of the endoscope shown in FIG. 1, light emitted from the tips of the fiber optic bundles 28 diverges to illuminate the field of view 32. Light reflected from objects in the field of view is collected by objective assembly 26, which forms an image in an image plane of the objects in the field of view. In the preferred embodiment, the image formed by objective assembly 26 is focused thereby on corresponding areas of the active surface of a CCD imaging element 34, which forms a CCD signal; that is, the active surface of the CCD element lies in the image plane. This CCD signal is preprocessed (principally preamplified) by electronics shown generally at 36. The CCD signal is transferred by cable 38 to control and post-processing electronics 40, generating a video signal driving a conventional video display unit 42 providing a visible image.

In an alternative embodiment, by arranging the plane of the image formed by the objective assembly 26 to coincide with the distal ends of a second bundle of optical fibers, the second bundle of fibers can be used to transfer the image to a CCD imaging element juxtaposed to their proximal ends. A relay lens may be interposed between the proximal ends of the fibers and the CCD element. Modification of the preferred embodiment in this way is considered to be within the skill of the art.

Returning to discussion of the illumination system, as discussed above it is an object of the invention to provide a sufficiently efficient optical system to allow employment of a relatively low cost light source, in particular a quartz-halogen lamp with integral reflector, as opposed to more costly short-arc xenon lamps, or the metal halide lamps shown in the Wood patent referred to above. According to the preferred embodiment, a fiber optic bundle 22 having a numerical aperture (NA) of approximately 0.66 is used in combination with the inventive objectives discussed herein, which exhibit light gathering power of between approximately f/4.5 and f/8. These components permit a relatively low cost quartz halogen lamp with integral ellipsoidal reflector, such as the GE Corporation ANSI type EFM lamp, to be used.

In addition to lamp 14 and reflector 16, a lens 44, e.g., Model 01-LPX-259 available from Melles-Griot, Irvine, Calif., may be provided to further focus light from lamp 14 onto the proximal ends 20 of the fibers of bundle 22. An infrared filter 46, e.g. Melles-Griot Model 03 FHA 043, may also be provided to reduce the amount of heat delivered to the distal tip of the endoscope.

As mentioned above, the prior art recognizes that it is necessary to provide dispersive optics juxtaposed to the distal tip of a fiber optic bundle used to carry light from a lamp at the proximal end of an endoscope cable to its tip, in order that light exiting the tip of the fiber optic bundle will be abruptly diverged, and illuminate a relatively wide field of view. The Ito and Nishioka patents referred to above, for example, show plano-concave and aspheric concave refractive optical members, respectively, for providing divergent optical properties. In certain cases these expedients may also be useful, for example, in connection with the novel objective optics of the present invention.

Figure 8:
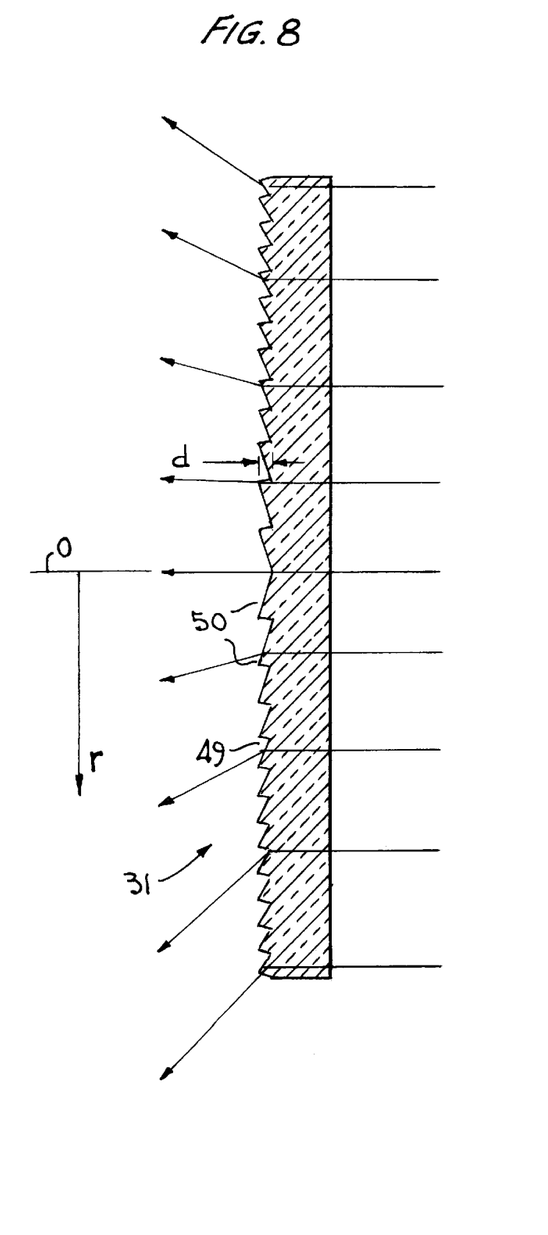
FIG. 8 shows a similar view of a diffractive optical element wherein only the groove spacing varies with radial position.

However, in the preferred embodiment of the endoscopic imaging system according to the present invention, a much less costly diffractive element 31 shown in schematic cross-sectional view in FIG. 8 is used to provide the divergent optical properties required. Light exiting the distal tips of fibers of fiber optic bundle 28 (not shown) exhibits moderate divergence with respect to their axes. This weakly diverging light is diffracted by concentric grooves of a circular transparent diffractive dispersing element 31 shown in cross-section; the light is caused to diverge uniformly radially outwardly, thus illuminating a relatively wide field of view.

By way of background, it is well-known that diffraction takes place when a light wave is incident on a sharp edge in the optical path; indeed, weakly diverging light exiting a very fine optical fiber, e.g., as used in telecommunications applications, will have its divergence increased somewhat by diffraction, i.e., without any divergent element, although this degree of divergence would be insufficient to illuminate a broad field of view. Similarly, conventional refractive optical elements are sometimes stated to be "diffraction-limited" when it is alleged that their optical performance cannot be improved further, i.e., that the inherent bending of light caused by diffraction limits their refractive performance.

According to the present invention, this inherent property of light is turned to advantage in that light is designedly bent by diffraction in addition to being bent solely by refraction, as is much the more common method of controlling the path of light rays.

As mentioned, numerous references discussed above provide theoretical background for optical designs using diffractive optics, and a number of patents referred to above provide concrete examples of optical diffractive elements as used for various purposes. However, no prior art of which the present inventors are aware shows use of a diffractive dispersive element for illuminating a wide field of view to be imaged by an endoscope, as shown in FIG. 8, nor as part of the objective of an endoscope, as discussed in detail below in the preferred embodiment.

As shown in FIGS. 1 and 2, two diffractive elements 31 are disposed on opposite sides of objective 60 to disperse light exiting the fiber optic bundles. Each element 31 comprises a circular member molded of acrylic plastic having a grooved surface 49 as illustrated in FIG. 8. In the embodiment disclosed in detail herein the diameter of surfaces 49 is 2.286 millimeters. Each grooved surface 49 includes a number of concentric grooves 50 of equal depth d, while the spacing of the grooves 50 decreases with radial distance r from the optical axis 0 of the diffractive element 31. The grooves 50 have angled side surfaces forming V- or "sawtooth"-shapes in section, as shown, thus comprising a "Kinoform" structure. Diffractive optical elements are also known having a "binary" structure, wherein the grooves are essentially square or rectangular in cross-section; "blazed" diffractive structures are also known, wherein the angled Kinoform grooves are approximated by step-like structures. See, e.g., the Faklis et al references discussed above.

The spacing of adjacent grooves 50 in the diffractive element 31 is on the order of between about 10 and about 100 times the wavelength of the light to be bent thereby; in the present case, white light of wavelength between about 450 and about 650 nanometers is to be diverged. The spacing of the grooves 50 can be expressed by a radial phase profile in waves wherein the phase shift $\phi(r)$ is described by the following equation:

$$\phi(r) = -0.20r^2 + 0.01r^4.$$

In this equation, the radius r is expressed in millimeters. The value for the phase shift $\phi(r)$ expresses the phase shift in millimeters that is experienced by an incident wave front. Alternatively, the phase shift $\phi(r)$ can be expressed in waves by dividing by the wavelength of light, in this case 0.0005876 mm. According to this equation, 417 waves of phase shift will be experienced over the total radius of 1.143 mm, with the phase shift varying with radial distance as indicated. The minimum spacing of the grooves is approximately 1.5 microns. The depth d of the grooves is approximately 1.2 microns. Such structures are now capable of being made by injection molding, which is accordingly the preferred method of manufacture of the diffractive dispersive elements 31.

The illuminator design is completed by two windows 33 (see FIG. 1) of fused silica or like high quality optical glass, protecting the diffractive surfaces 49 of elements 31.

It will be apparent to those of skill in the art that elements 22, 28 may be fabricated from various appropriate light-conductive materials, and need not necessarily comprise fiber-optic elements. For example, elements 22, 28 may be solid extruded polymer members, or may be tubular shells filled with light-conductive liquid or gel materials, or combinations thereof. It will be further appreciated that elements 22, 28 may be separable from the main body of the endoscope.

As mentioned above, several different designs for the objective 26 are shown in FIGS. 3–6. The designs shown in FIGS. 3, 4, and 5 each include a number of plastic elements; diffractive surfaces may be molded thereon, or provided in other ways discussed below, while the FIG. 6 design is an all-glass refractive design. The FIG. 6 design achieves the optical goals of the objective of the invention, but at relatively higher cost than the diffractive designs of FIGS. 3–5.

Figures 3, 4:
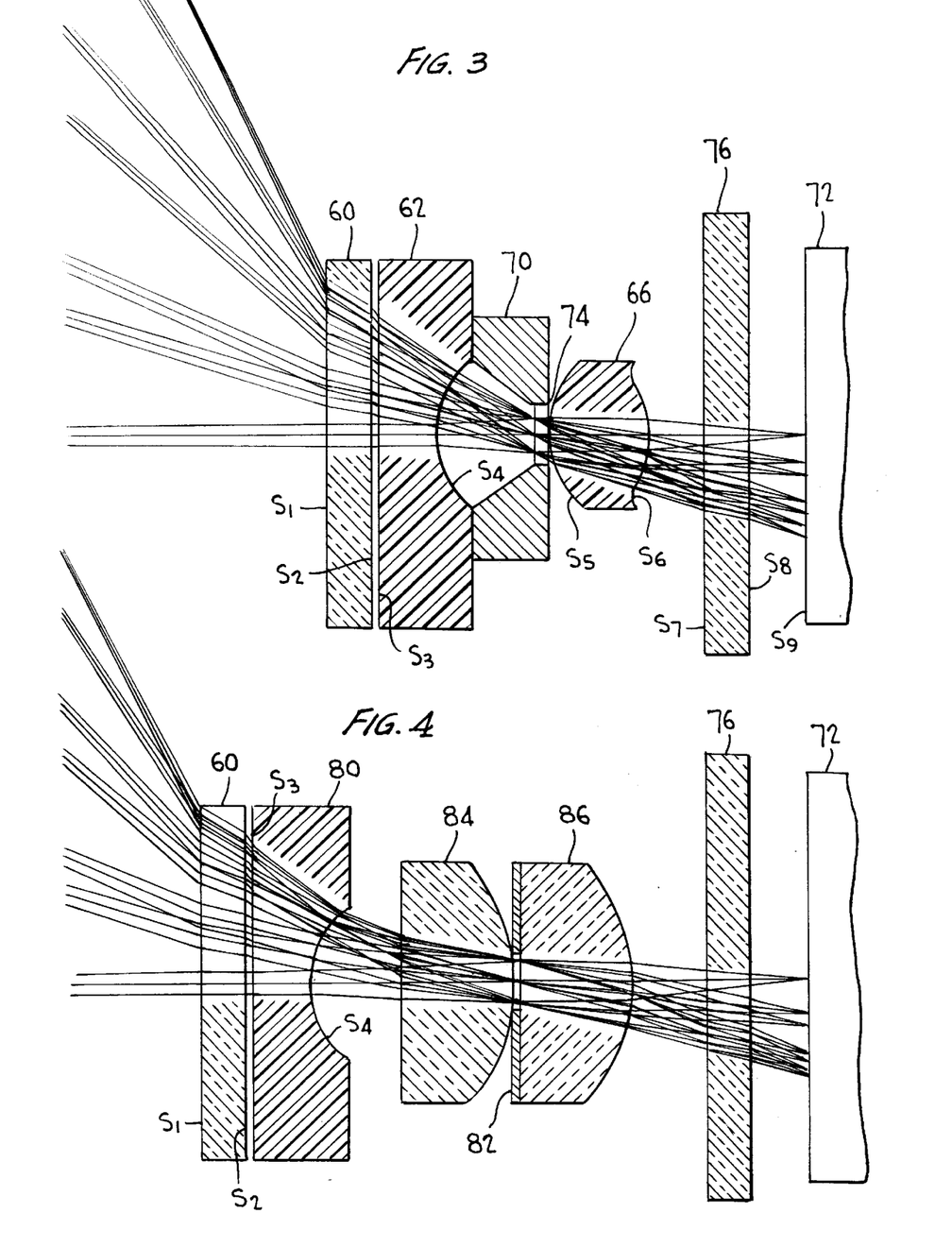
FIG. 3 shows a schematic cross-sectional view of the objective according to the invention in a first embodiment thereof.
FIG. 4 shows a similar view of a second embodiment of the objective.

Turning first to the FIG. 3 design, which is currently the preferred embodiment of the objective of the invention, light reflected from objects at left is received from a field of view having a half angle of 67.5°, for a total field of view of 135°. The outermost component of the objective is a plano glass window 60 having no optical power. Window 60 protects the distal optical element 62, using the phrase "optical element" in this specification to refer only to elements having refractive and/or diffractive optical power.

Figure 7:
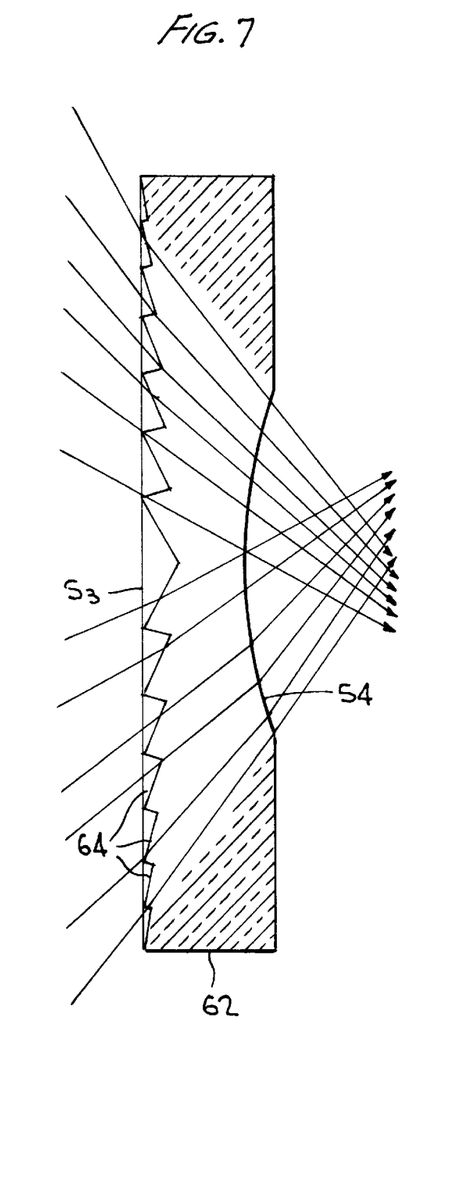
FIG. 7 shows a schematic cross-sectional view of a diffractive optical element wherein both the spacing and depth of grooves in the element vary with radial position.

In this embodiment, the diffractive surface is provided on the distal surface $S_3$ of plano-concave element 62, that is, on the surface juxtaposed to window 60. A schematic view of element 62 is shown in FIG. 7. As there illustrated, the grooves 64 in this element are both deeper and more widely spaced at the center of the optical element, unlike the dispersive diffractive element 31 of FIG. 8, wherein the depth of the grooves is constant across the surface of the element. The detailed optical specifications of the grooves 64 are given below in connection with those of the remaining components of the objective. The other surface $S_4$ of element 62 is spherical concave, as shown in FIG. 3.

Referring to FIG. 3, juxtaposed to optical element 62 is an aperture stop 70 which may be molded of black polycarbonate plastic or other light absorptive material in the frustoconical shape shown; alternatively, the pupil 74 of the aperture stop 70 can be provided by a circular hole in a circular element.

The function of aperture stop 70 is to limit the light passing through the diffractive surface $S_3$ so that only light from specified regions of the field of view is imaged on the corresponding picture elements ("pixels") of the CCD imaging array 72. In an important aspect of the invention, pupil 74 of the aperture stop is disposed a distance at least equal to its diameter from the diffractive surface $S_3$. A one-to-one relationship between the pixels on the CCD imaging array 72 and the corresponding areas of the field of view is thus provided, which is essential in order that an image can be formed; that is, aperture stop 70 ensures that light from any single object point can only intercept a limited portion of the diffractive surface.

The proximal optical element 66 is also molded of an optical grade of acrylic plastic and has a spherical distal surface $S_5$ and an aspherical proximal surface $S_6$. Surfaces $S_5$ and $S_4$ may also be aspheric if a higher relative aperture is required. The objective design shown in FIG. 3 is completed by a plano glass window 76, typically provided as part of the CCD imaging array 72. A further option is to provide the diffractive surface on surface $S_2$ of the distal window, e.g. by epoxy film replication techniques generally known in the art. A diffractive surface can also be provided on either of surfaces $S_7$ or $S_8$ of window 76, using a similar technique.

Referring to the detailed optical specification of the preferred embodiment of the objective, the spacing of the grooves 64 formed in surface $S_3$ of element 62, as illustrated in FIG. 7, may be described in terms of the phase difference $\phi(r)$ imparted to light by the following equation:

$$\phi(r) = 0.014817r^2 - 0.00019152r^4$$

As discussed above in connection with the equation describing the dispersive diffractive element of FIG. 8, this equation describes the location of the grooves by specification of the phase differences imparted to light thereby. In this equation, the radial distance r is given in millimeters, as is the phase shift $\phi(r)$. To express the phase difference in waves, one divides the phase shift $\phi(r)$ by the wavelength, selected in this case to be 0.000535 mm. For example, at r=2.0 mm, the phase shift is 0.056 mm, or 105 waves.

Iterative calculation methods show that the first groove is at a radial distance of 0.19006 mm from the optical axis, the second at a distance of 0.26885 mm, and the third at 0.32935 mm; the next to last groove is at 1.98934 mm, and the last 1.99943 mm. Hence, the separation between adjacent grooves varies between 0.07879 mm, between the first and second grooves, and 0.01009 mm, at the radial outermost edge of the element. The minimum groove spacing is thus 0.01009÷0.000535=18.85 wavelengths. The fact that the closest spaced grooves are spaced by on the order of twenty wavelengths allows so-called "scalar" mathematical techniques to be used to model performance of the lens. More specifically, if the grooves were significantly closer, e.g. less than 10 wavelengths, more complex mathematics would be required to calculate precisely the bending effect exerted.

As noted, the groove depth function for the element 62 is such that the grooves 64 are deepest in its center. In the example given, the groove depth d(r) in microns varies according to the following equation:

$$d(r)=1.0809-0.091485r-0.071423r^2.$$

Accordingly, the depth of the grooves at the center is 1.0829 microns, and decreases over the 2 mm radius of element 62 to 0.6122 microns at the outer edge of element 62.

It will be apparent to those of skill in the art that while precise coefficients are given in the equations above for groove width and spacing, in fact, these can vary through rather substantial ranges without affecting use of the invention for the purposes described. Essentially, the spacing of the grooves 64 should be between about 10 and about 100 times the wavelength of the light; accordingly, the invention should not be limited to the precise coefficients shown.

In addition to the equation given above for the phase sgift φ(r), the location of the grooves can be solved to a very close approximation using the following equation:

$$r(m)=[2mf\lambda/n+(m\lambda/n)^2]^{1/2}$$

wherein:

r(m) is the radius of the m-th groove, i.e., m is an integer identifying the groove number, counting from the optical axis;

f is the focal length of the diffractive surface;

λ is the center wavelength of the light with which the element is intended to be used; and n is the refractive index of the material of the element.

The depth of these grooves again varies as described as above, that is, as a function of radius.

It will also be recognized by those of skill in the art that element 62 also refracts light. The refractive bending is measured by the refractive index of the material of which element 62 is molded, the thickness of element 62 at its center, and the radius of the spherical concave surface $S_4$, In the example given, element 62 is molded of optical grade acrylic plastic, equivalent to Rohm and Haas V920 or V811, its central thickness is 1.016 mm, and the radius of surface $S_4$ is 1.651 mm. Element 62 can be injection molded in a simple operation in a mold having the "negative" of grooves 64 diamond turned into one mating surface and the spherical surface formed in the other mating surface.

Providing the optical prescription of the remaining components in the FIG. 3 embodiment of objective 26, proximal element 66 is also injection molded of the same optical grade acrylic plastic. Surface $S_5$ is spherical with a radius of 1.744 nm while surface $S_6$ is aspherical with the sagitta z(r) (that is, the departure of the surface from a plane shape) given by profile equation:

$$z(r)=-0.610694r^2/[1+(1+0.166711r^2)^{1/2}]+0.01019928r^4+0.0627469r^6.$$

At its center, proximal element 66 is 1.651 mm thick.

Windows 60 and 76 are made using the usual optical glasses, e.g. Schott SF11, are both 0.762 mm thick, and may be provided with anti-reflection coatings to ensure maximum transmissivity of the light received.

The pupil 74 of the aperture stop may be configured as the central hole in a spacer; in the example given, this should be 0.610 mm in diameter. The aperture stop should be made of light absorptive material, e.g., molded of black polycarbonate or the like.

The optical prescription of the objective of FIG. 3 is completed by specification of the spacing of the various elements from one another. Surface $S_4$ of element 62 is 1.667 mm from the pupil 74 of the aperture stop, which in turn is 0.254 mm from the distal surface $S_5$ of element 66. Proximal surface $S_6$ of element 66 is 1.016 mm from surface $S_7$ of window 76. Window 76 may be provided as an integral component of CCD element 72.

Again, those of skill in the art will recognize that a useful objective according to the invention could be realized despite considerable variation from the detailed optical prescription given, and will recognize accordingly that the invention should not be limited thereby.

FIG. 4 shows a second embodiment of the objective of the endoscope of the invention. In this case, windows 60 and 76 are generally as described above, as is the CCD imaging array 72. A plano-concave molded plastic distal element 80 is again provided, having a diffractive outer surface $S_3$ generally as above, although the optical prescription may vary somewhat. An aperture stop 82 having a pupil disposed well away from the diffractive surface is again provided. However, in this case, an additional medial glass element 84 is provided. The optical specifications of medial element 84 may be identical to a modified plano-convex proximal element 86, as shown. The aperture stop 82 defining the minimum diameter of the bundle of rays is located between elements 84 and 86; the aperture stop may be provided as a coating of opaque material (e.g. aluminum, with an appropriate anti-reflective coating) on the planar surface of distal element 86, with a center hole left transparent forming a pupil of the desired diameter. As suggested above with respect to other embodiments, the diffractive surface might alternatively be provided on the proximal surface $S_4$ of element 80, and surface $S_4$ might again be aspherical.

Figure 5:
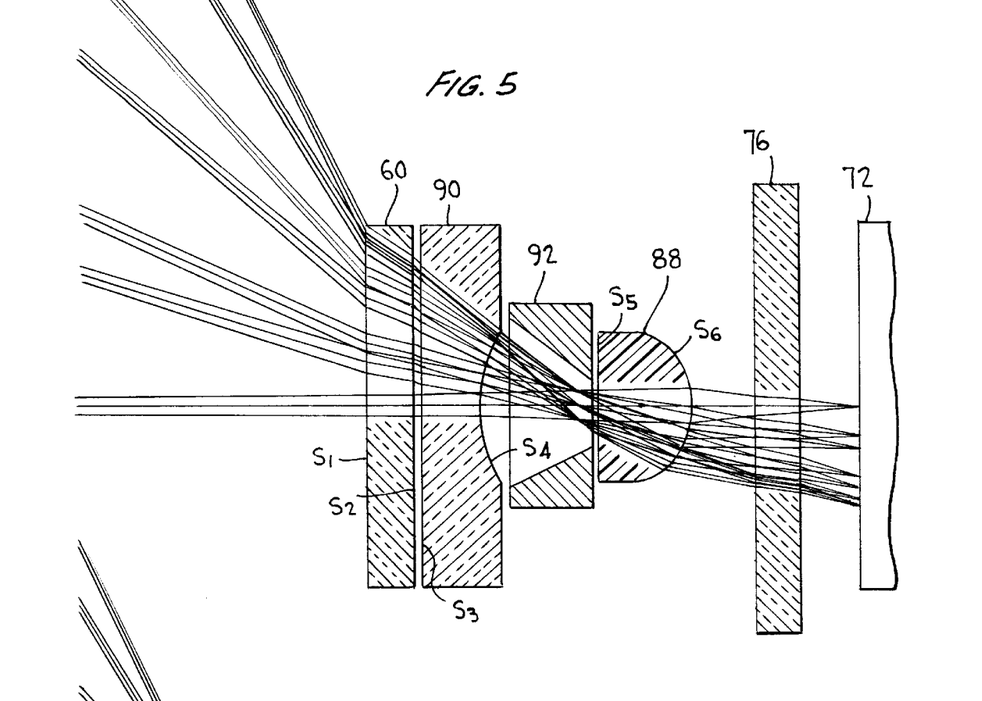
FIG. 5 shows a similar view of a third embodiment of the objective.

FIG. 5 shows a further embodiment, wherein windows 60 and 76 and CCD imaging array 72 are again generally as described above in connection with FIG. 3. However, in this embodiment, the diffractive surface having grooves of varying depth and spacing is provided on the proximal spherical surface $S_6$ of the plano-spherical proximal element 88; the plano-concave element 90 does not include a diffractive surface. Again, an aperture stop 92 is disposed between proximal element 88 and distal element 90, and is spaced well away from diffractive surface $S_6$, allowing an image to be formed.

In addition to the various modifications and alternatives shown and described specifically above, note that the diffractive surfaces formed on surfaces $S_3$ of the embodiments of FIGS. 3 and 4 could be formed on surfaces $S_2$ of the corresponding windows 60. Similarly, a diffractive surface could also be provided on a distal surface of window 76. In both cases, these diffractive surfaces can be provided by suitably patterned resin films applied to the glass windows.

It is also within the scope of the invention, where not excluded by the claims which follow, to provide objectives conforming generally to the optical designs shown in FIGS. 3–5 above, and possibly further modified in ways that will be apparent to those of skill in the art, but avoiding the diffractive surfaces discussed.

Figure 6:
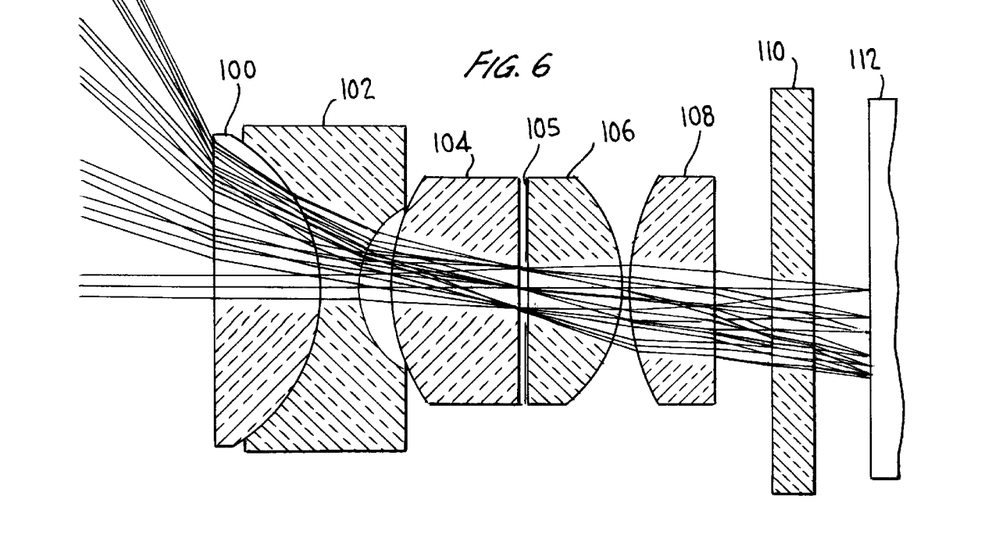
FIG. 6 shows a similar view of an all-glass objective according to the invention.

FIG. 6 shows an objective also sufficiently fast and radially compact to be useful with the remainder of the endoscopic imaging system according to the invention, but employing only glass elements formed using known polishing techniques, and not including a diffractive element. The FIG. 6 objective is less compact and more expensive than the objectives using molded plastic components having optical power and diffractive surfaces as described above, and therefore is less preferred as of the filing of this application. Nonetheless, as indicated, the all-glass objective design of FIG. 6 is suitable for formation of a useful image when combined with the remaining components of the endoscopic imaging system according to the invention, and therefore is to be considered to be within the claims of this application where not explicitly excluded thereby.

As will be appreciated by those of skill in the art, the all-glass objective of FIG. 6 includes a distal plano-convex element 100, a bi-concave element 102, a second plano-convex element 104 having a surface closely juxtaposed to a third plano-convex element 106, and a fourth plano-convex element 108. In this design, the aperture stop 105 is formed on one of the closely juxtaposed plano surfaces of elements 104 and 106, and may comprise an aluminum or other metallic film, with an appropriate anti-reflective coating, having a central aperture of the appropriate pupil diameter formed therein. The objective is completed by a plano glass window 110, as above, which is juxtaposed to or forms a part of CCD imaging element 112.

Given the above description of the novel aspects of the FIGS. 4–6 design forms, preparation of detailed optical prescriptions corresponding to the design forms shown in FIGS. 4–6 is within the ordinary skill of the art.

FIG. 7, as discussed above, shows in highly schematic form the plano-concave element 62 of the preferred embodiment of the objective shown in FIG. 3; similar elements would be employed in the FIGS. 4 and 5 objectives. FIG. 7 illustrates, again in highly schematic form, the variation in depth and spacing of the grooves 64 formed with respect to the plano surface. These grooves are illustrated as being formed beneath a generally planar surface, so that their "peaks" lie on a line. Equivalently, the grooves could be disposed above a plano reference surface, i.e., such that the "troughs" of the grooves would lie on a straight line. The Kino-form grooves shown could be replaced with binary or "blazed" grooves, as discussed above. Again, and as noted above, while two different formulas for defining the variation in the spacing of the grooves 64 in the element 62 are given above, it is to be understood that these are only exemplary of numerous optical prescriptions useful in implementation of the particular objective design detailed above, and that the invention is not to be limited thereby.

FIG. 8 was also discussed above, and shows the diffractive dispersive element 31 employed in the preferred embodiment of the illuminator to cause the weakly divergent light emitted by the fiber optic bundles to diverge strongly, so as to illuminate objects in a broad field of view, and such that light reflected therefrom can be collected by the objective to form an image on the active surface of the CCD imaging element. As discussed above, the prior art shows use of various refractive dispersive optical elements; the diffractive element shown is much lighter and more compact, and less expensive in quantities sufficient to amortize the mold tooling required.

It will therefore be appreciated that there has been described an improved endoscope wherein diffractive optical elements may be used in either or both of the objective and the illumination system. Employment of diffractive optics in the objective allows the objective to be small, compact, and relatively low cost, while employment of diffractive optics in the illuminator further reduces cost, thus enabling the construction of an endoscope of improved optical characteristics in a package of reduced physical size and at lower cost than available in the prior art. In particular, the use of diffractive optics provides a very fast objective, allowing the use of a relatively low cost halogen lamp as the light source.

While a preferred embodiment of the invention, including a number of different embodiments of the objective, has been shown and described in detail, this should not be taken as a limitation on the invention, which is to be limited only by the appended claims.

What is claimed is:

1. An objective for an endoscope, said objective intended to form an image in an image plane, said objective comprising:

a first distal optical element, adapted to be disposed between an object and an aperture stop, an aperture stop, for absorbing rays of light passing through portions of said distal optical element other than from corresponding predetermined portions of the object, and a second proximal optical element, adapted to be disposed between said aperture stop and an imaging element, wherein:

a number of grooves spaced from one another by between about 10 and about 100 wavelengths of visible light are formed on at least one of distal or proximal surfaces of said distal and proximal optical elements, constituting said surface a diffractive surface;

said at least one diffractive surface is spaced well away from said aperture stop, said aperture stop being located with respect to said diffractive surface and having a pupil diameter such that only rays incident on particular limited areas on the diffractive surface from said corresponding predetermined portions of the object can reach corresponding points on the imaging surface; and the depth and spacing of the grooves in said at least one diffractive surface varying with radial distance from the optical axis.

2. The objective of claim 1, wherein the grooves in said at least one diffractive surface are deeper and more widely spaced toward the optical axis thereof.

3. The objective of claim 1, wherein said distal optical element is plano-concave.

4. The objective of claim 3, wherein said plano-concave distal optical element is molded of homogenous index of refraction acrylic plastic.

5. The objective of claim 3, wherein said grooves are molded into one of the distal planar or proximal spherical surfaces of said plano-concave distal optical element, constituting said surface a diffractive surface.

6. The objective of claim 5, wherein said grooves are molded into the distal planar surface of said plano-concave distal optical element.

7. The objective of claim 6, wherein the spacing of said grooves varies as a function of radius r from the optical axis of said plano-concave distal optical element such that light at a wavelength of 535 nm experiences a phase shift $\phi(r)$ in mm varying as a function of radius, also in mm, as defined by the following equation:

$$\phi(r)=0.014817r^2-0.00019152r^4.$$

8. The objective of claim 7, wherein the depth d(r) of said grooves in microns is described as a function of radius in mm from the optical axis by the following equation:

$$d(r)=+1.0809-0.091485r-0.071423r^2.$$

9. The objective of claim 6, wherein said grooves are located at radial distances r(m) in mm from the optical axis of said plano-concave distal optical element described by the following equation:

$$r(m)=[2mf\lambda/n+(m\lambda/n)^2]^{1/2}$$

wherein:
m is an integer identifying the groove number, counting from the optical axis;
f is the focal length of the diffractive surface;
λ is the center wavelength of the light with which the element is intended to be used; and
n is the refractive index of the material of the element.

10. The objective of claim 9, wherein the depth d(r) of said grooves in microns is described as a function of radius in mm from the optical axis by the following equation:

$$d(r)=+1.0809-0.091485r-0.071423r^2.$$

11. The objective of claim 6, wherein said proximal optical element is also molded of homogenous index of refraction acrylic plastic.

12. The objective of claim 11, wherein said proximal element has a spherical convex distal surface and an aspheric proximal surface.

13. The objective of claim 11, wherein the pupil of said aperture stop is juxtaposed to said distal surface of said proximal optical element.

14. The objective of claim 1, wherein a further medial optical element is provided between said aperture stop and said distal element.

15. The objective of claim 14, wherein said further medial and proximal elements are of identical configuration.

16. The objective of claim 15 wherein said medial and proximal elements are plano-convex.

17. The objective of claim 15, wherein said medial and proximal elements are of glass.

18. The objective of claim 1, wherein the distal surface of said proximal element is convex spherical, and the proximal surface of said proximal element is aspheric.

19. The objective of claim 1, wherein said diffractive surface is provided on either the proximal or distal surface of said distal element.

20. The objective of claim 1, wherein the outermost component of the objective is a piano window.

21. The objective of claim 20, wherein a number of grooves are disposed on the proximal planar surface of said window, constituting said proximal surface a diffractive surface.

22. The objective of claim 1, further comprising a plano window disposed between said proximal element and said imaging element.

23. The objective of claim 22, wherein a number of grooves spaced between about 10 and about 100 times the wavelength of visible light are disposed on either the distal or proximal planar surface of said window, constituting said surface a diffractive surface.

24. An endoscopic imaging system, comprising:
a probe having proximal and distal ends;
a light source juxtaposed to said proximal end of said probe;
said probe comprising an optical conduit carrying light from said light source to said distal tip of said probe,
dispersive optics at said distal tip of said probe, for illuminating a field of view;
an objective lens assembly at said distal tip of said probe, for collecting light from said field of view and forming an image thereof;
a solid-state imaging element for generating an output image signal responsive to light collected by said objective lens assembly; and
display means for displaying a visible image responsive to said output image signal;
wherein a number of grooves of radial dimensions between about 10 and about 100 times the wavelength of visible light are molded into an optical surface of one or both of said dispersive optics and objective lens assembly, constituting said surface a diffractive optical element.

25. The endoscopic imaging system of claim 24, wherein said objective lens assembly comprises:
a first distal optical element, adapted to be disposed between an object and an aperture stop,
an aperture stop, for absorbing rays of light passing through portions of said distal optical element other than from corresponding predetermined portions of the object, and
a second optical element, adapted to be disposed between said aperture stop and said imaging element, and wherein:
at least one diffractive surface is provided on one of distal and proximal surfaces of said distal and proximal optical elements; and
said at least one diffractive surface is spaced well away from said aperture stop, said aperture stop being located with respect to said diffractive surface and having a pupil diameter such that only rays incident on particular limited areas on the diffractive surface from said corresponding predetermined portions of the object can reach corresponding points on the imaging surface.

26. The endoscopic imaging system of claim 25, wherein said distal optical element is plano-concave, and said grooves are molded into one of the distal planar and proximal spherical surfaces of said plano-concave distal optical element, constituting said surface a diffractive surface.

27. The endoscopic imaging system of claim 26, wherein the depth and spacing of grooves in said at least one diffractive surface vary with radial distance from the optical axis.

28. The endoscopic imaging system of claim 27, wherein the grooves in said at least one diffractive surface are deeper and more widely spaced toward the optical axis thereof.

29. The endoscopic imaging system of claim 28, wherein the spacing of said grooves varies as a function of radius r from the optical axis of said plano-concave distal optical element such that light at a wavelength of 535 nm experiences a phase shift φ(r) in mm varying as a function of radius, also in mm, as defined by the following equation:

$$\phi(r)=0.014817r^2-0.00019152r^4.$$

30. The endoscopic imaging system of claim 29, wherein the depth d(r) of said grooves in microns is described as a function of radius in mm from the optical axis by the following equation:

$$d(r)=-1.0809+0.091485r+0.071423r^2.$$

31. The endoscopic imaging system of claim 28, wherein said grooves are located at radial distances r(m) in mm from the optical axis of said plano-concave distal optical element described by the following equation:

$$r(m)=[2mf\lambda/n+(m\lambda/n)^2]^{1/2}$$

wherein:
- m is an integer identifying the groove number, counting from the optical axis;
- f is the focal length of the diffractive surface;
- $\lambda$ is the center wavelength of the light with which the element is intended to be used; and
- n is the refractive index of the material of the element.

32. The endoscopic imaging system of claim 31, wherein the depth d(r) of said grooves in microns is described as a function of radius in mm from the optical axis by the following equation:

$$d(r)=-1.0809+0.091485r+0.071423r^2.$$

33. The endoscopic imaging system of claim 26, wherein said proximal element has a spherical convex distal surface and an aspheric proximal surface.

34. The endoscopic imaging system of claim 33, wherein the pupil of said aperture stop is juxtaposed to said distal surface of said proximal optical element.

35. The endoscopic imaging system of claim 25, wherein a medial optical element is provided between said aperture stop and said distal element.

36. The endoscopic imaging system of claim 35, wherein said medial and proximal elements are of identical configuration.

37. The endoscopic imaging system of claim 26, wherein said medial and proximal elements are plano-convex.

38. The endoscopic imaging system of claim 25, wherein said distal surface of said proximal element is convex spherical, and the proximal surface of said proximal element is aspheric.

39. The endoscopic imaging system of claim 25, wherein said diffractive surface is provided on the distal surface of said proximal element.

40. The endoscopic imaging system of claim 24, wherein said light source comprises a halogen lamp with associated power supply, and an essentially ellipsoidal reflector focusing light from said lamp substantially onto a proximal end of said optical conduit.

41. The endoscopic imaging system of claim 40, further comprising a plano-convex lens disposed between said reflector and said proximal end of said fiber optic conduit for further concentrating light thereon.

42. The endoscopic imaging system of claim 24, wherein said fiber optic conduit comprises two fiber optic bundles having a common proximal input end juxtaposed to said reflector, and diverging to be juxtaposed to plural dispersive optics disposed at the distal tip of said probe.

43. The endoscopic imaging system of claim 24, wherein said dispersive optics comprises a diffractive optical element.

44. The endoscopic imaging system of claim 24, wherein said solid-state imaging element is juxtaposed directly to said objective lens assembly.

45. An illumination system for an endoscopic probe, comprising a light source for juxtaposition to the input end of an optical conduit, and a dispersive element juxtaposed to the output end of said conduit at a distal tip of said probe, said light source comprising a halogen lamp with associated power supply and an ellipsoidal reflector focusing light from said lamp on a proximal end of said fiber optic conduit, and said dispersive element comprising a diffractive optical element.

46. The illumination system of claim 45, further comprising a plano-convex lens disposed between said reflector and said proximal end of said optical conduit, for further concentrating light thereon.

47. The illumination system of claim 45, wherein said optical conduit comprises two fiber optic bundles having a common proximal input end juxtaposed to said reflector, and diverging to be juxtaposed to plural dispersive optics disposed at the distal tip of said probe.

48. The illumination system of claim 45, wherein said diffractive optical element comprises a transparent member having a number of grooves formed therein having substantially consistent depth and spacing on the order of between about 10 and about 100 times the wavelength of visible light.

49. An endoscopic imaging system, comprising;
(1) an illumination system, comprising (a) an optical conduit having a proximal input end and a distal output end, (b) a light source comprising a halogen lamp with associated power supply and an ellipsoidal reflector focusing light from said lamp substantially onto a proximal end of said optical conduit, and (c) a diffractive dispersive element juxtaposed to said distal output end of said conduit at a distal tip of an endoscopic probe;
(2) an image formation portion, including (a) an objective disposed at said distal tip of an endoscopic probe, and comprising at least one diffractive surface for collecting light from a field of view, and (b) a solid-state imaging element for forming an image signal responsive to light collected by said objective; and
(3) an image processing and display portion, including (a) signal processing circuitry for converting said image signal to a video signal, and (b) a display device responsive to said video signal for displaying an image responsive to said light collected from said field of view.

50. The imaging system of claim 49, wherein said image formation portion further comprises preprocessing circuitry for amplifying said CCD signal.

51. The imaging system of claim 49, wherein said objective further comprises an aperture stop defining a pupil spaced from said diffractive surfaces by a distance at least equal to the diameter of said pupil.

52. The imaging system of claim 49, wherein said a solid-state imaging element is juxtaposed directly to said objective.

53. The imaging system of claim 49, wherein the numerical aperture of said optical conduit is at least about 0.66.

* * * * *